(12) United States Patent
Kinsella

(10) Patent No.: US 9,970,925 B2
(45) Date of Patent: May 15, 2018

(54) IN VIVO REPORTER SYSTEM

(75) Inventor: Todd M. Kinsella, Redwood City, CA (US)

(73) Assignee: RIGEL PHARMACEUTICALS, INC., South San Francisco, CA (US)

( * ) Notice: Subject to any disclaimer, the term of this patent is extended or adjusted under 35 U.S.C. 154(b) by 563 days.

(21) Appl. No.: 13/825,542

(22) PCT Filed: Sep. 26, 2011

(86) PCT No.: PCT/US2011/053299
§ 371 (c)(1),
(2), (4) Date: May 28, 2013

(87) PCT Pub. No.: WO2012/044586
PCT Pub. Date: Apr. 5, 2012

(65) Prior Publication Data
US 2014/0150124 A1    May 29, 2014

Related U.S. Application Data

(60) Provisional application No. 61/388,453, filed on Sep. 30, 2010.

(51) Int. Cl.
| | | |
|---|---|---|
| *A61K 48/00* | (2006.01) |
| *C12N 15/00* | (2006.01) |
| *C07H 21/04* | (2006.01) |
| *G01N 33/50* | (2006.01) |
| *C12Q 1/68* | (2018.01) |
| *C12N 15/10* | (2006.01) |
| *C12N 15/79* | (2006.01) |

(52) U.S. Cl.
CPC ..... *G01N 33/5061* (2013.01); *C12N 15/1055* (2013.01); *C12Q 1/6897* (2013.01); *C07H 21/04* (2013.01); *C07K 2319/92* (2013.01); *C12N 15/79* (2013.01); *C12N 2510/00* (2013.01); *C12N 2800/00* (2013.01); *C12N 2800/10* (2013.01)

(58) Field of Classification Search
CPC ................ C12N 15/79; C12N 2510/00; C12N 2800/00; C12N 2800/10; C07H 21/04
USPC .......... 424/93.21; 435/320.1; 536/23.4, 23.7, 536/24.1
See application file for complete search history.

(56) References Cited

U.S. PATENT DOCUMENTS

| | | | |
|---|---|---|---|
| 6,551,786 B2 | 4/2003 | Manfred |
| 2002/0106688 A1* | 8/2002 | Jenboubi |
| 2003/0194809 A1 | 10/2003 | Yadav et al. |
| 2004/0172688 A1* | 9/2004 | Yadav et al. |

FOREIGN PATENT DOCUMENTS

| | | |
|---|---|---|
| WO | WO199832325 | 7/1998 |
| WO | WO2008008874 | 1/2008 |

OTHER PUBLICATIONS

Kanno, et al., "Intein-mediated reporter gene assay for detecting protein-protein interactions in living mammalian cells.", Anal Chem. Jan. 15, 2006;78(2):556-60.

* cited by examiner

*Primary Examiner* — Shin Lin Chen
(74) *Attorney, Agent, or Firm* — James S. Keddie; Carol L. Francis; Travis Young

(57) ABSTRACT

A construct system for expressing a reporter protein, as well as a transgenic animal and a screening method employing the same, are provided. In certain embodiments, the construct system is a three component system in which expression of a reporter protein from a reporter construct is induced by a transcription factor that is produced using two other constructs, each producing a different part of the transcription factor. The parts of the transcription factor are ligated together. Expression of the reporter only occurs in tissues in which both of the parts of the transcription factor are produced.

13 Claims, 4 Drawing Sheets

Reporter construct

First transcription factor construct

Second transcription factor construct

IN VIVO REPORTER SYSTEM

CROSS-REFERENCING

This application claims the benefit of U.S. provisional application Ser. No. 61/388,453, filed on Sep. 30, 2010, which application is incorporated by reference herein for all purposes.

BACKGROUND

Transgenic and/or knock-in animals engineered for in vivo imaging often employ specific promoters capable of receiving various signals and converting those signals into transcriptional outputs.

However, many of such promoters suffer from overall weak induction levels to the point that signal to noise ratios are not sufficiently high to achieve good quality data. This can be especially problematic when the tissues in which a reporter functions is located deep within the animal's body. Furthermore, whole animal imaging that is based on luminescence or fluorescence can be stymied by signal interference that arises when a promoter has residual activity in a surrounding tissue such as skin. In certain cases, a residual expression level of 2-4% can be enough to hamper accurate results.

Certain aspects of this disclosure relate to a reporter system that can, in some embodiments, mitigate the drawbacks described above.

SUMMARY

A construct system for expressing a reporter protein is provided. In certain embodiments, the system comprises: a) a reporter construct comprising: i. an inducible promoter that is activated by a transcription factor; and ii. a coding sequence encoding a reporter protein, wherein the coding sequence is in operable linkage with the inducible promoter; b) a first transcription factor construct comprising: i. a first promoter; and ii. a coding sequence encoding a first fusion protein comprising a first portion of a transcription factor and a first subunit of a split intein, wherein the coding sequence is in operable linkage with the first promoter; and c) a second transcription factor construct comprising: i. a second promoter; and ii. a coding sequence encoding a second fusion protein comprising a second portion of the transcription factor and a second subunit of the split intein, wherein the coding sequence is in operable linkage with the second promoter; wherein expression of the first and second fusion proteins in a cell results in ligation, by the first and second subunits of the split intein, of the first and second portions of the transcription factor to produce the transcription factor.

In some embodiments, the first and second promoters have overlapping expression patterns. In particular embodiments, the system provides for expression of the transcription factor (and reporter protein) only in regions in which expression of the promoters overlaps.

The first and second promoters may be, independently, tissue restricted, conditionally-inducible, constitutive, or temporally expressed promoters. In one embodiment, at least one of the promoters may be tissue-restricted. In another embodiment, at least one of the promoters may be conditionally inducible.

In some embodiments, the transcription factor may have a portion of the GAL4, VP16 or the tetracycline activator and, in particular embodiments, the promoter that is activated by the transcription may comprise at least one binding site for GAL4 or the tetracycline activator.

In some embodiments, at least two of the constructs are present on the same or different vector.

In particular embodiments, the reporter protein may be optically detectable, e.g., a luciferase or a fluorescent protein.

A cell comprising the constructs system is also provided. In particular embodiments, the cell may be any animal cell, e.g., a mammalian cell.

A screening method is also provided: In certain embodiments, this method comprises: a) contacting the cell described above with a candidate agent; and b) observing the expression of the reporter protein by the cell. The cell may be a cultured cell that is present in vitro, or a cell that is present in a multi-cellular organism in vivo.

A transgenic non-human animal is also provided. The animal may comprise a genome comprising the constructs system described above. The animal may be a mammal, e.g., a murine.

The transgenic animal may be employed in a screening assay. In general terms, this method comprises administering a candidate agent to the transgenic animal; and determining if the candidate agent affects expression of the reporter protein. In certain cases, this method may comprise exposing the transgenic animal a stimulus to induce one or more promoters in a tissue of the animal. In particular embodiments, the method may comprise exposing the transgenic animal to a muscle atrophy-inducing stimulus, thereby producing the reporter protein only in muscle tissue that is undergoing atrophy.

The candidate agent may be an RNA (e.g., an inhibitory RNA or an RNA that encodes a protein) or an organic molecule of less than 2500 Da in molecular weight, for example.

BRIEF DESCRIPTION OF THE DRAWINGS

In FIG. 1B, "TF1" and "TF2" are the first and second portions of a transcription factor, respectively and "$1^{st}$ intein" and "$2^{nd}$ intein" are the first and second subunits of an intein, respectively.

DEFINITIONS

Figure 1A:
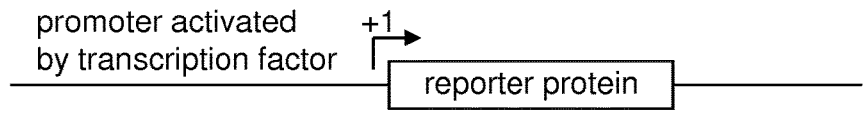
FIGS. 1A and 1B schematically illustrates some features of a subject reporter system.
Figure 1A:
Figure 1A:
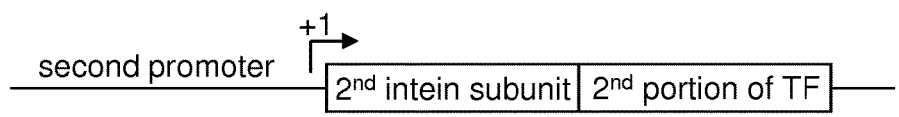

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Determining the presence of" includes determining the amount of something present, as well as determining whether it is present or absent.

The term "contacting" means to bring or put together. As such, a first item is contacted with a second item when the two items are brought or put together, e.g., by touching them to each other or combining them in the same solution.

The phrase "optical signal" refers to light signal that can be detected by a photodetector, e.g., a light microscope, a spectrophotometer, a fluorescent microscope, a fluorescent sample reader, or a fluorescence activated cell sorter, 3D tomographer, a camera, etc.

The term "optically detectable protein" refers to a protein whose expression can be detected by the presence of an optical signal produced by the protein. An optical signal is produced by a protein, for example, when the protein is capable of being excited by a particular wavelength of light and emits another wavelength of light which is detectable. An optical signal is produced by a protein, for example, when the protein catalyzes a reaction which results in a light signal. Fluorescent proteins, luminescent proteins, etc., are examples of optically detectable proteins.

The term "gene" refers to a nucleic acid sequence comprised of a promoter region, a coding sequence, and a 3'UTR.

The terms "protein" and "polypeptide" are used interchangeably herein.

A "signal sequence" is a sequence of amino acids present at the N-terminal portion of a protein which facilitates the secretion of the mature form of the protein from the cell. The definition of a signal sequence is a functional one. The mature form of the extracellular protein lacks the signal sequence, which is cleaved off during the secretion process.

The term "nucleic acid" encompasses DNA, RNA, single stranded or double stranded and chemical modifications thereof. The terms "nucleic acid" and "polynucleotide" are used interchangeably herein.

A "non-human" animal refers to any mammal of a species that is not human.

The terms "rodent" and 'rodents' refer to all members of the phylogenetic order Rodentia including any and all progeny of all future generations derived therefrom.

The term "murine" refers to any and all members of the family Muridae, including rats and mice.

The term "progeny" or "off-spring" refers to any and all future generations derived and descending from a particular animal. Thus, progeny of any successive generation are included herein such that the progeny, the F1, F2, F3, generations and so on are included in this definition.

The phrase "transgenic animal" refers to an animal comprising cells containing foreign nucleic acid (i.e., recombinant nucleic acid that is not native to the animal). The foreign nucleic acid may be present in all cells of the animal that contain a genome, or in some but not all cells of the animal. The foreign nucleic acid molecule is called a "transgene" and may contain one or many genes, cDNA, etc. By inserting a transgene into a fertilized oocyte or cells from the early embryo, the resulting transgenic animal may be fully transgenic and able to transmit the foreign nucleic acid stably in its germline. Alternatively, a foreign nucleic acid may be introduced by transferring, e.g., implanting, a recombinant cell or tissue containing the same into an animal to produce a partially transgenic animal that is somatically transgenic.

The term "introns" refers to sequences of DNA found in the middle of many gene sequences in most eukaryotes. These intron sequences are transcribed, but removed from within the pre-mRNA transcript before the mRNA is translated into a protein. This process of intron removal occurs by self-splicing of the sequences (exons) on either side of the intron.

The term "operably-linked" refers to the association of nucleic acid sequences on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). Similarly, when an IRES is operably-linked to a coding sequence, the IRES provides for translation of the mRNA transcribed from that coding sequence. Another example of operably linked sequence is the when a sequence is present in the 3'UTR of a gene. This sequence is operably linked to the promoter region of that gene. Two elements that are operably linked includes two elements that are in tandem as well as one element inserted into the other. "Unlinked" means that the associated genetic elements are not closely associated with one another and the function of one does not affect the other.

When two elements are "co-expressed", they are induced at the same time and repressed at the same time. The levels at which two proteins are co-expressed need not been the same for them to be co-expressed.

The term "homozygous" indicates that identical alleles reside at the same loci on homologous chromosomes. In contrast, "heterozygous" indicates that different alleles reside at the same loci on homologous chromosomes. A transgenic animal may be homozygous or heterozygous for a transgene.

The term "luciferase" refers to an enzyme that emits light during the oxidation of its substrate luciferin. The terms luciferin and luciferase do not refer to a particular luciferin or luciferase. They are generic terms for a substrate and its associated enzyme (or protein) that catalyzes a light-producing reaction.

The phrase "in vivo imaging" as used herein refers to methods of detecting the presence of an optically detectable protein in whole, live animal. Optically detectable proteins such as fluorescent proteins and luciferases may be detected by in vivo imaging. In vivo imaging may be used provide 2-D as well as 3-D images of an animal. Charge-coupled device cameras, CMOS, or 3D tomographers may used to carry out in vivo imaging.

The term "induced" with respect to a promoter, is intended to encompass both the initiation of transcription of a downstream nucleic acid, as well as an increase in the rate of transcription of a downstream nucleic acid that is already being transcribed, compared to an uninduced state.

The term "endogenous" with reference to a gene, indicates that the gene is native to a cell, i.e., the gene is present at a particular locus in the genome of a non-modified cell. An endogenous gene may be a wild type gene present at that locus in a wild type cell (as found in nature). An endogenous gene may be a modified endogenous gene if it is present at the same locus in the genome as a wild type gene. An example of such a modified endogenous gene is a gene into which a foreign nucleic acid is inserted. An endogenous gene may be present in the nuclear genome, mitochondrial genome etc.

The term "biologically active", with respect to a gene or protein, refers to a gene or protein that has a biological activity. So-called "knock-outs" are not biologically active. If an altered gene or protein is referred to as being biologically active, then it has significantly the same activity of an unaltered version of the gene or protein. No significant change in phenotype may be observed in an animal having biologically active altered gene relative to an unaltered gene.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "construct" refers to any polynucleotide that contains a recombinant nucleic acid. A construct may be present in a vector (e.g., a viral vector) or may be integrated in a genome, for example.

The term "selective marker" refers to a protein capable of expression in a host that allows for ease of selection of those hosts containing an introduced nucleic acid or vector. Examples of selectable markers include, but are not limited to, proteins that confer resistance to antimicrobial agents (e.g., hygromycin, bleomycin, or chloramphenicol), proteins that confer a metabolic advantage, such as a nutritional advantage on the host cell, as well as proteins that confer a functional or phenotypic advantage (e.g., cell division) on a cell.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "candidate agent" is intended to encompass oligonucleotides, polynucleotides, siRNA, shRNA genes, gene products, polypeptides, small molecules, e.g., up to 2500 Dalton (Da) in size, and pharmacological compounds that are combined with the cells or the animals described herein to screen for an effect. In certain cases, a candidate agent may be delivered as a nucleic acid that is transcribed and/or translated to provide the candidate agent, for example, a RNAi molecule or a polypeptide.

The term "coding sequence" refers to a nucleic acid sequence that once transcribed and translated produces a protein, for example, in vivo, when placed under the control of appropriate regulatory elements. A coding sequence as used herein may have a continuous ORF or might have an ORF interrupted by the presence of introns or non-coding sequences. In this embodiment, the non-coding sequences are spliced out from the pre-mRNA to produce a mature mRNA.

The phrase "muscle cell", as used herein, refers to muscles cells of all kinds, such as, mature muscle cells, including skeletal, smooth and cardiac muscle cells, precursors of these muscle cells, any intermediate cell existing during the differentiation of a muscle precursor cell, muscle fibers, muscle cell lines, etc. Examples of muscle cells include myoblasts, myotubes, myocytes, cardiac muscle cells, skeletal muscle cells, myofibers etc. Muscle cell may be present in vivo (in an animal) or in vitro (in a cell culture).

The phrase "secreted reporter enzyme" refers to an enzyme that is secreted from the cell producing it and that enzyme serves as a reporter in that it is detectable by an enzyme assay of, for example, cell culture medium, body fluids, such as, blood, lymph, etc.

The phrase "translational shunt sequence" refers to a nucleic acid sequence which codes for a peptide that provides for separation of two proteins joined by the peptide. Translational shunt sequences are found in a variety of organisms, such as viruses. Translational shunt sequences are useful for generating separate proteins co-translationally, i.e., translational shunt sequences encode peptides that provide for production of two proteins from a single mRNA. A translational shunt sequence is usually situated in frame between two ORFs, encoding two proteins or polypeptides, forming a single ORF. Translational shunt sequences have been described in Trichas (*BMC Biology*, 6: 40, 2008) de Felipe (*Genet. Vaccines Ther.* 2: 13, 2004) and El Amrani (*Plant Physiol.* 135:16-24, 2004), which are incorporated by reference for their disclosure of translational shunts.

The phrase "atrogen gene" refers to a gene whose expression is induced in muscle cells exposed to an atrophy-inducing stimulus (e.g., fasting, etc) prior to a detectable muscle atrophy phenotype i.e., a detectable loss of muscle mass, shriveling of cells, etc., is observable.

The phrase "atrogen promoter" refers a promoter that is induced in muscle cells exposed to an atrophy-inducing stimulus (e.g., fasting, etc) prior to a detectable muscle atrophy phenotype i.e., a detectable loss of muscle mass, shriveling of cells, etc., is observable. An atrogen promoter may be the promoter of a wild type atrogen gene, or an active variant thereof that is, for example, at least 95% identical to a wild type atrogen promoter.

The terms "muscle cell atrophy", "muscle atrophy" and "atrophy" are used interchangeably to refer to muscle cell atrophy in vitro or in vivo. Muscle cell atrophy, in vivo, refers to a decrease in the mass of a muscle, fiber size, cross-sectional area, etc. A decrease in the mass of the muscle is usually accompanied with a weakening of the muscles. Muscle cell atrophy, in vitro, refers to muscle cell shriveling, muscle cell death, etc. The terms "muscle cell atrophy", "muscle atrophy" and "atrophy" are used to refer to atrophy caused by a variety of stimuli, unless stated otherwise. Thus, muscle atrophy refers to atrophy due to fasting, cachexia, diabetes, etc.

The term "intein" refers to an enzyme that is capable of catalytically splicing two proteins together in cis or in trans. Inteins are known in the art and are reviewed in a number of publications, including Paulus (Annual Review of Biochemistry, 2000, 69: 447-496), Paulus (Chemical Society Reviews 1998 27:375-386), Paulus (Bioorganic Chemistry 2001 29:119-129) and published U.S. patent applications 20040014100 and 20030013148. A comprehensive list of inteins and description of their biology may be found at New England Biolabs Intein Database (InBase Reference: Perler, F. B. (2002). InBase, the Intein Database. Nucleic Acids Res. 30, 383-384), as found at the world wide website of New England Biolabs.

A "split intein" is an intein that is made up of two subunits (which are arbitrarily defined herein as a "first subunit" of an intein and a "second subunit" of an intein) that, together, form a catalytically active enzyme that splices protein. A split intein may be a naturally split intein (the subunits of which may be expressed as two distinct proteins in an organism) or an artificially split intein (in which cases an intein that is not already split may be split and expressed as two subunits, which, together, form a catalytically active enzyme). The construction and use of split inteins to join proteins together is known. See, e.g., Aranko (PLoS One. 2009; 4:e5185), Dassa (Nucleic Acids Res. 2009 37:2560-73), Appleby (J. Biol. Chem. 2009 284:6194-9), Ludwig (J. Biol. Chem. 2008 283: 25264-72), Sun (J. Biol. Chem. 2004 279:35281-6), and Liu (J. Biol. Chem. 2003 278:26315-8) among many others.

Intein-containing genes can be broken into two fragments within the intein domain, and still create the mature protein product by a trans-protein splicing reaction (i.e. protein ligation). Each of the broken genes codes for a separate polypeptide: one consisting of the N-terminal part of the host followed by the N-terminal part of the intein, and the other consisting of the C-terminal part of the intein followed by the C-terminal part of the host. The two intein parts, termed 'split-intein', associate tightly and specifically with each other leading to a protein-splicing reaction, which ligates the two host protein parts in trans. Protein-splicing is typically a robust and rapid reaction, needing no cofactors or external energy sources. Split-inteins can be engineered synthetically, but also occur naturally. Split-inteins were readily created in the lab from different natural contiguous inteins, with several different breaking points.

A "transcription factor" is a protein that binds to a specific DNA sequence in a promoter and controls the initiation or repression of transcription from that promoter. The amino acid sequence of a transcription factor may be arbitrarily divided into two portions (which are arbitrarily defined herein as a "first portion" and a "second portion" of a transcription factor). When present alone (i.e., without the other portion) or together in an unligated form, the first and second portions of a transcription factor do not bind to a specific DNA sequence in a promoter and control the initiation or repression of transcription from that promoter. When the first and second portions of a transcription factor are ligated together, a protein that binds to a specific DNA sequence in a promoter and control the initiation or repression of transcription from that promoter is produced.

A promoter that is "tissue restricted" is a promoter that is active in one or more tissue or organ (e.g., in muscle and skin, bone and pancreas, brain and hair follicles, for example). A promoter that is "tissue specific" is a type of tissue restricted promoter that is active in a single tissue or organ (e.g., muscle, skin, bone, pancreas, for example).

A promoter that is "conditionally-inducible" is inducible in response to a stimulus, e.g., a physiological, environmental or chemical stimulus.

A promoter that is "temporally-expressed" is active during a particular period of time, e.g., only during a defined period in development.

A promoter that is "constitutive" is active in substantially every tissue under all conditions.

As would be apparent, certain promoters are, for example, tissue specific as well as conditionally inducible. As such, the promoter types listed above are not mutually exclusive from each other.

DESCRIPTION OF EXEMPLARY EMBODIMENTS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of cells and reference to "a candidate agent" includes reference to one or more candidate agents and equivalents thereof known to those skilled in the art, and so forth. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Construct Systems

Provided herein is a three-component construct system for expressing a reporter protein. An exemplary embodiment of the construct system is illustrated in FIG. 1A. With reference to FIG. 1A, the exemplary construct system comprises: a) a reporter construct containing a promoter that is activated by a transcription factor, operably linked to a coding sequence for a reporter protein (e.g., an optically detectable protein or a detectable enzyme), and b) two constructs (which are arbitrarily designated as the first transcription factor construct and the second transcription factor construct in FIG. 1A) that, when expressed in the same cell, produce a transcription factor that binds to the promoter and induces expression of the reporter protein.

As illustrated in FIG. 1A, the first transcription factor construct contains i. a first promoter; and ii. a coding sequence in operable linkage with the first promoter, encoding a first fusion protein comprising a first portion of a transcription factor and a first subunit of a split intein. Likewise and as illustrated in FIG. 1A, the second transcription factor construct contains i. a second promoter; and ii. a coding sequence in operable linkage with the second promoter, encoding a second fusion protein comprising a second portion of the transcription factor and a second subunit of the split intein. As will be described in greater detail below, the promoters in the first and second constructs may be different, and they are not activated by the encoded transcription factor. The first and second fusion proteins may, independently, have the intein subunits positioned C- or N-terminally. As illustrated in FIG. 1A, the first fusion protein may contain an intein sequence at the C-terminal end, and the second fusion protein may contain an intein sequence at the N-terminal end, although other configurations are possible.

Figure 1B:
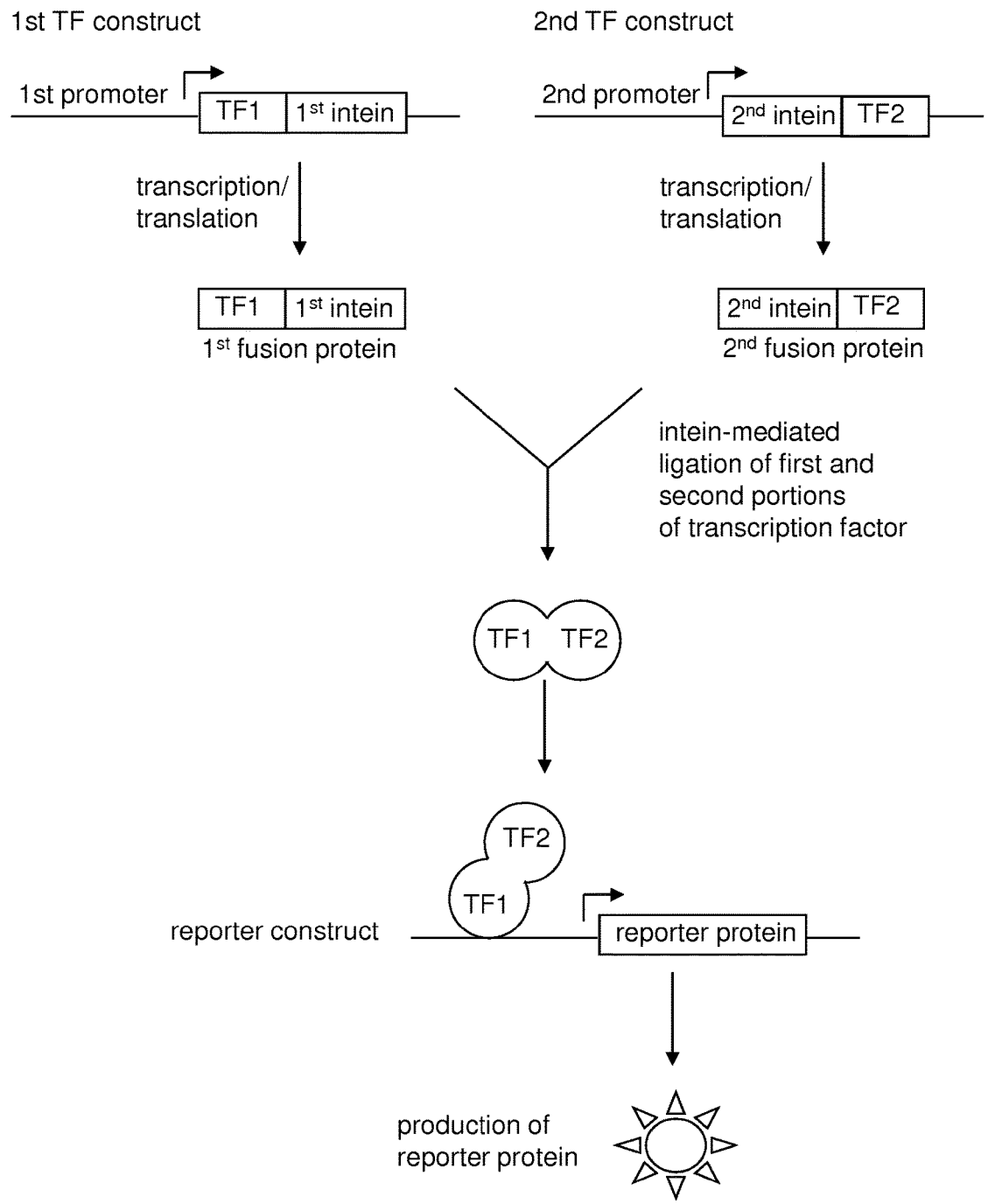

As illustrated in FIG. 1B, expression of the first and second fusion proteins in a cell results in intein-mediated ligation of the first and second portions of the transcription factor by the first and second subunits of the split intein (i.e., the ("1$^{st}$ intein" and "2$^{nd}$ intein", respectively) to produce the transcription factor, which, in turn, activates expression of the reporter protein encoded by the reporter construct. Specifically and as illustrated in FIG. 1B, if the first and second promoters are active in a cell, then the first and second fusion proteins are produced. The first and second portions of the transcription factor (TF1 and TF2) are joined together in a ligation reaction catalyzed by the first and second subunits of the intein, thereby producing a transcription factor that binds to and induces expression of the reporter construct. Thus, the reporter protein is produced only in cells in which the first promoter and the second promoter are active.

The use of a transcription factor to induce production of the reporter protein provides an amplification of the signal produced by the reporter protein, relative to a system that does not employ a transcription factor. Moreover, the system allows the reporter protein to be expressed only in cells in which both promoters are active. The system may be employed to, for example, restrict expression of the reporter protein in a transgenic to only those tissues in which both promoters are active. While there is no requirement that the promoters that drive the expression of the fusion proteins be different, in certain embodiments the promoters are different to one another in that they have different expression patterns. In particular embodiments, a first promoter that is classified as a tissue restricted, conditionally-inducible, temporally-expressed or constitutive promoter may be employed in one reporter construct (i.e., the first or the second reporter construct) and a different promoter that may be of the same class or different class as the first promoter may be employed in the other reporter construct. In an exemplary embodiment, a tissue restricted promoter may be used in combination with a conditionally inducible promoter to provide stimulus-inducible expression of the reporter protein that is restricted to a particular tissue. In another exemplary embodiment, a tissue restricted promoter may be used in combination with a different tissue restricted promoter to provide expression of the reporter protein only tissues in which expression of the promoters overlap. For example, a promoter that is active in bladder, blood, bone, bone marrow, brain, cervix, colon, eye, heart, kidney, larynx, liver, lung, lymph node, mammary gland, muscle, ovary, pancreas, peripheral nervous system, placenta, prostate, skin, small intestine, soft tissue, spleen, stomach, testis, thymus, tongue, or uterus, or any sub-tissue thereof (see, e.g., Liu BMC Bioinformatics. 2008 9:271) may be employed in one of the reporter constructs, and a stimulus-inducible promoter that is induced during, e.g., atrophy, aging, apoptosis, an inflammatory response, pathogen infection or any other phenotype associated with a particular disease or condition may be employed in the other reporter construct, thereby providing inducible expression that is restricted to a particular tissue and avoiding problems associated with the use of "leaky" promoters and tissue non-specific promoters.

As is well recognized in the art, inteins typically are composed of two domains (termed herein the first subunit and second subunit herein) that can be naturally (in the case of the Ssp DnaE intein, for example) or non-naturally (i.e., artificially or by recombinant means, for example) present as two different molecules. These intein domains, when present together, can reconstitute an active intein, and can be used to join two different polypeptides together in trans or in cis. The construction and use of split inteins to join proteins together is known. See, e.g., Aranko (PLoS One. 2009; 4:e5185), Dassa (Nucleic Acids Res. 2009 37:2560-73), Appleby (J. Biol. Chem. 2009 284:6194-9), Ludwig (J. Biol. Chem. 2008 283: 25264-72), Sun (J. Biol. Chem. 2004 279:35281-6), and Liu (J. Biol. Chem. 2003 278:26315-8) among many others.

Naturally-occurring intein-mediated protein splicing proceeds according to one of two pathways, a classical and alternative pathway depending on which particular intein is used. Naturally-occurring inteins that catalyze splicing using the classical pathway, such as many of those listed above, typically contain a N-terminal Cys or Ser amino acid as an intein reactive site. Naturally-occurring inteins that catalyze splicing using the alternative pathway, such as the M. jannaschii KlbA intein, and others, typically use an N-terminal Ala amino acid as an intein reactive site. Almost all naturally-occurring inteins contain a Ser, Cys or Thr amino acid as a C-terminal intein reactive site. Accordingly, in performing the subject methods, a wide variety of amino acids may be chosen for use at intein-reactive sites.

An intein may be of bacterial, yeast, mammalian or viral origin, for example. Accordingly and without wishing to limit the invention to any particular intein, exemplary inteins for use in the subject methods include: the Ssp DnaB intein from *Synechocystis* spp. strain PCC6803, the Mxe GyrA intein from *Mycobacterium xenopi*, the CIV RIR1 intein from *Chilo* iridescent virus, the Ctr VMA intein from *Candida tropicalis*, the Gth DnaB intein from *Guillardia theta*, the Ppu DnaB intein from *Porphyra purpurea*, the Sce VMA intein from *Saccharomyces cerevisiae*, the Mfl RecA intein from *Mycobacterium flavescens*, the Ssp DnaE intein from *Synechocystis* spp. strain PCC6803, the Mle DnaB intein from *Mycobacterium leprae*, the Mja KlbA intein from *Methanococcus jannaschii*, the Pfu KIbA from *Pyrococcus furiosus*, the Mth RIR1 intein from *Methanobacterium thermoautotrophicum* (delta H strain), the Pfu RIR1-1 intein from *Pyrococcus furiosus*, the Psp-GBD Pol intein from *Pyrococcus* spp. the GB-D, Thy Pol-2 intein from *Thermococcus hydrothermalis*, the Pfu IF2 intein from *Pyrococcus furiosus*, Pho Lon intein from *Pyrococcus horikoshii* OT3, the Mja r-Gyr intein from *Methanococcus jannaschii*, the Pho RFC intein from *Pyrococcus horikoshii* OT3, the Pab RFC-2 intein from *Pyrococcus abyssi*, the Mja RtcB (Mja Hyp-2) intein from *Methanococcus jannaschii*, the Pho VMA intein from *Pyrococcus horikoshii* OT3, the Mtu RecA intein, the PI-pfuI intein and the PU-pfu II intein, and artificial trans-splicing variants thereof.

Reporter Constructs

The promoter used in the reporter construct should be activatable by the transcription factor encoded by the first and second constructs. While any defined promoter that can be activated by a transcription factor may be used in the reporter construct, in certain cases the promoter used may contain a binding site for the tet, lac or Gal4 transcription factors, which have all been employed to activate reporter in conjunction with an exogenously added transcription factor in various transgenic systems (see, e.g., Mallo Front. Biosci. 2006 11:313-27). In particular embodiments, the promoter used may have multiple binding sites for the transcription factor used. In certain embodiments, the promoter used should have no basal level of activity in the absence of the transcription factor used.

As noted above, the reporter protein may be an optically detectable (e.g., a luciferase and a fluorescent protein) or a detectable enzyme, although other reporter proteins, e.g., colorigenic reporters, may be used under certain circumstances.

In certain cases the reporter protein may be a cyan fluorescent protein, a yellow fluorescent protein, a green fluorescent protein, a red fluorescent protein, a blue fluorescent protein, or any mutant thereof, including mutants of ECFP, EYFP, EGFP, ERFP, EBFP, obtained by enhancing the fluorescence intensity. Such reporter proteins may be derived from the fluorescent proteins of *Aequorea, Discoma, Ptilosarcus*, or *Renilla* GFP, for example, which proteins are well known.

Alternatively, derivatives based upon the luciferase family proteins, most commonly firefly (*Photinus pyralis*) and *Renilla reniformis*, can produce a luminescent signal that is detectable in a microscopy imaging environment. Luciferase used in the present disclosure may be derived from, e.g., the *Renilla* (protein accession no. CAA01908), firefly (protein acc. No. CAA59282), click-beetle (protein acc. No. AAQ19142), G. princes luciferase (GLUC), or other sources of luciferase. Luciferase used in the present disclosure cover mutated and otherwise modified versions such as mammalian codon optimized luciferases. Methods for using luciferases for real-time imaging of luciferase expression in live animals have been described (L. F. Greer, et al., Luminescence 17: 43-74, 2002). Luciferase, from various sources, has been used in various assays and reporting capacities. For example, U.S. Pat. No. 6,387,675 discloses the use of the luciferase gene of click beetle, *P. plagiophthalamus*, in eukaryotic cells for biosensing.

In another embodiment, the reporter protein does not produce a fluorescent or luminescent signal directly, but rather enzymatically converts an undetectable (e.g., non-fluorescent) substrate to an optically detectable (e.g., fluorescent) product. Commonly used enzymes include B-galactosidase, horseradish peroxidase, alkaline phosphatase, B-glucuronidase, B-lactamase, chloramphenicol acetyltransferase. A wide array of substrates for fluorescence and luminescence detection are available commercially (Sigma, Invitrogen).

In some embodiments, the reporter construct may comprise a coding sequence for a first optically detectable protein and a second coding sequence for a secreted reporter enzyme. A number of secreted reporter enzymes, such as, secreted alkaline phosphatase (SEAP), may be used. An enzyme that may be modified, for example, by addition of a secretion signal peptide and assayed by a reliable assay may be used. SEAP has been extensively used to measure promoter/enhancer activity and has been used as an in vivo reporter, see, e.g., Gene 66, 1-10, 1988, Mets. Enzymol. 216, 362-368, 1992, Nilsson E. E., et al., *Cancer Chemother. Pharmacol.*, 49: 93-100, 2002, Westfall S. D. and Skinner M. K., *Mol Cancer Ther* 2005, 4(11), etc. Kits and instructions for measuring SEAP are available, for example, from Applied Biosystems, Clontech, etc. In these embodiments, a reporter construct may comprise a translational shunt sequence present between two coding sequences. Translational shunt sequences are well known in the art and are discussed in a number of references, e.g., Trichas G. et al., *BMC Biology,* 6: 40, 2008, de Felipe P., *Genet. Vaccines Ther.* 2(1): 13, 2004, El Amrani A. et al., *Plant Physiol.* 135(1):16-24, 2004, etc. Translational shunt sequences provide a way to separate several proteins encoded from a single mRNA, for example, in a polycistronic construct. Translational shunt sequences such as those encoding 2A peptides result in the cotranslational "cleavage" of proteins.

First and Second Transcription Factor Constructs

As noted above, the promoters used in the first and second transcription factor construct may be, independently, any of a wide variety of promoters. Likewise, the fusion proteins encoded by the first transcription factor construct contains a portions of any of a wide variety of transcription factors and intein subunits, which are generally described above The transcription factor that is split between the first and second fusion proteins may be any suitable transcription factor. Such transcription factors may contain a DNA binding domain that binds to the promoter used in the reporter construct, and an activation domain that interacts with an RNA polymerase to activate transcription of the coding sequence of the reporter construct. Since the DNA binding and activation domains of a transcription fact are modular in sense that the activation domain of a transcription factor can often be swapped with other activation domains and remain functional, a variety of different transcription factors can be used. In certain embodiments, the transcription factor contains a GAL4, tet or lac DNA binding domain operably linked to a heterologous activation domain, e.g., from GAL4, VP16 or E1A, although other configurations are possible. The amino acid sequence of the transcription factor is apportioned between the first and second constructs in a way that ensures that: a) neither of the portions alone or in the same cell but not ligated together, activate transcription of the reporter construct, and b) when the first and second portions of a transcription factor are ligated together, the product activates transcription of the reporter protein. In one exemplary embodiment, one of the fusion proteins may contain a DNA binding domain of a transcription factor and the other may contain the transcription activation domain of the transcription factor, although other configurations are possible.

In certain cases, one or more of the promoters used in the first and second transcription factor constructs is a promoter that is induced during muscle atrophy. In certain embodiments, the promoter used in at least one of the transcription factor constructs may be a promoter of a E3 ubiquitin ligase. In particular embodiments, the promoter used may be the promoter of the Ub ligase (E3) Atrogin-1, also named Muscle Atrophy F-box (MAFbx). In certain embodiments, the promoter used may be the promoter of Muscle RING Finger 1 (MuRF1), which is also an E3 ligase. MAFbx and MuRF1 were identified as universal markers/mediators of muscle atrophy as the expression of these genes was up-regulated in a variety of animal models of muscle atrophy and animals lacking a functional MAFbx or MuRF1 gene were resistant to denervation induced muscle atrophy (Bodine S. C. et al., *Science* 294, 1704-1708, 2001, Gomes M. D. et al., *Proc. Natl. Acad. Si. USA* 98, 14440-14445, 2001). These genes are up-regulated early during the atrophy process and at least in the fasting induced animal model of atrophy, the increase in MAFbx precedes loss of muscle weight.

In certain embodiments, the promoter used in at least one of the transcription factor constructs may be the promoter of a metallothionein-1L, metallothionein-1B, or FoxO1. These genes, in addition to playing a role in initiating muscle cell atrophy may also play a role in maintenance of muscle in an atrophied state. These genes are described in, e.g., Sacheck J. M. et al., *FASEB J.,* 21, 140-155, 2007. In certain aspects, the promoter may be that of may be lipin, TG interacting factor, or AMP deaminase. These genes are up-regulated at the initiation of the muscle cell atrophy program.

These and other promoter that could be used in the transcription factor constructs are been described in a number of research publications and reviews, for example, in Sacheck J. M. et al., *FASEB J.,* 21, 140-155, 2007; Lecker S. H. et al. *FASEB J.,* 18, 39-51, 2004; Jagoe R. T. et al. *FASEB J.* 16, 1697-1712, 2002, Gomes M. D. et al., *Proc. Natl. Acad. Sci. USA* 98, 14440-14445, 2001; Bodine S. C. et al., *Science* 294, 1704-1708, 2001, etc. The genes that are disclosed in these publications as being specifically up-regulated upon initiation of muscle cell atrophy are herein incorporated by reference.

In additional embodiments, any muscle-specific promoter may be employed (e.g., the muscle creatine kinase (MCK) promoter, the smooth muscle alpha-actin (SMAA) promoter, the Pitx3 gene promoter, the mef2c promoter or the C5-12 promoter, among many others).

The three constructs described above may be, independently, present on an isolated vector outside of a cell, present on a vector that autonomously replicates within a cell, or present on a vector that does not replicate within a cell. In certain embodiments, one or more of the constructs may be present in the genome of a cell. The cell may be of any species (e.g., bacterial, yeast, plant or animal, such as an insect, fish, amphibian, bird, reptile or mammalian cell). If the cell is a mammalian cell, the cell may be from any mammal, including rat, mouse, monkey and human etc. The constructs need not be present on different DNA molecules. For example, in certain embodiments, the constructs may be all present on the same vector (or at the same locus in a genome) and in other embodiments, the constructs may be present on different vectors (or at different loci in a genome).

Isolated Cells and Transgenic Animals

As noted above, the coding sequences for the first and second transcription factor constructs are operably linked to the promoter used in those constructs. In certain embodiments, the construct may be assembled in a vector outside of a cell, and introduced into the cell. In particular embodiments, the construct may integrated into the cell's genome at a random or targeted site. In other embodiments, the coding sequence for the fusion protein may be site-specifically integrated into the genome of the cell, thereby placing the expression of the fusion protein under the control of a promoter that is endogenous to the cell. This approach may be done using a so-called "knock-out" strategy (which, for example swaps the endogenous coding sequence for a gene with the coding sequence for the fusion protein and thereby results in an inactivated locus) or a so called "knock-in" strategy that inserts the coding sequence for a fusion protein into a gene in a way in which the gene maintains its ability to produce an endogenous protein that is biologically active, as well as the reporter protein.

In knock-in embodiments, the coding sequence for the fusion protein may be inserted either at the 3' end of the coding sequence or the 3' UTR of an endogenous gene, and the coding sequences separated by, for example, an IRES or a translational shunt sequence. The constructs may be integrated into the genome of the cell using any method. In certain embodiments, zinc-finger nucleases may be employed, as described in Geurts et al (*Knockout rats via embryo microinjection of zinc-finger nucleases.* Science. 2009 325:433); Durai et al (*Zinc finger nucleases: custom-designed molecular scissors for genome engineering of plant and mammalian cells.* Nucleic Acids Res. 2005 33:5978-90) and Porteus et al (Gene targeting using zinc finger nucleases. Nat. Biotechnol. 2005 23:967-73).

The constructs may be introduced into a cell by any known method, e.g., by transfection by a viral vector, e.g., a lentiviral or retroviral vector. In certain cases, at least one of the constructs may be inserted via homologous recombination. In certain cases, the presence of the reporter construct does not disrupt the cell's ability to respond to a stimulus that is going to be employed in the screening assay in which the cell is to be used.

The subject cell may be any cell. In particular embodiments, the cell may an ES cell, a myoblast, a myotube, muscle fiber, etc. A number of cell lines as well as methods for introducing nucleic acid into cells are known in the art. The stem cells may be obtained from any mammalian species, e.g. human. In exemplary embodiments, a muscle cell line may be used, such as, SM3, Aza2, BC3H-1, BD1, BD2, BD10, C2C12, TD33, TD38, TD45, TG1, C2, HL-1, AT-1, etc.

A subject cell may be cultured in vitro, under appropriate culture conditions. In some embodiments, the cell may be cultured in vivo, for example in a particular organ, tissue in an animal. In certain embodiments, the cell may be cultured ex vivo, for example in a particular organ, tissue of an animal. In other embodiments, the cell may be implanted in a particular region of an animal, e.g., in a skeletal muscle, producing a transgenic animal that comprises cells comprising a subject reporter construct which may, in certain embodiments, be present in atrogen gene.

The transgenic non-human animal may be mammalian, such as, equine, bovine, porcine, canine, feline, rodent, etc. In some embodiments the mammal is a murine, e.g. a mouse or rat.

In some embodiments, the transgenic animal may be generated from an ES cell. In this embodiment, all cells of the animal may have the reporter construct. For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce gene-targeted animals. See U.S. Pat. Nos. 5,387,742; 4,736,866; and 5,565,186; and Larson et al. (2000) *Mol. Ther.* 2:631-639 for methods of making gene-targeted animals. After transformation, the cells are plated onto a feeder layer in an appropriate medium. Cells containing the reporter construct may be detected by employing a selective medium. After sufficient time for colonies to grow, they are picked and analyzed for the occurrence of homologous recombination of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for cells having the construct. By providing for a different phenotype of the blastocyst and the ES cells, chimeric progeny can be readily detected. The chimeric progeny is further breeded to identify those that have germ-line cells having the construct. Animals having a heterozygous alteration are generated by breeding of chimeras. Male and female heterozygotes are typically bred to generate homozygous animals.

In some embodiments, the animal model is generated by implanting a subject cell into an animal. In this case, the animal model is a transgenic animal that comprises cells comprising the reporter construct. The cell may be an ES cell, a myotube, a myoblast, etc. The cell may be implanted to any of the muscles of the animal including but not limited to cardiac muscle, skeletal muscle, etc.

Methods of Screening

A method using the cell and animal described above for identifying agents that modulate promoter activity is provided. In exemplary embodiments, the method involves contacting a subject cell, described above, with a candidate agent, and determining the effect, if any, of the candidate agent on the production of the reporter protein encoded by the reporter construct. In some embodiments, the method involves contacting an animal containing the constructs described above with a candidate agent, and determining the effect, if any, of the candidate agent on production of the reporter protein by the animal. The cell or animal may be additional exposed to conditions that induce one or more of the promoters of the first and second constructs, thereby allowing the identification of agents that inhibit the stimulus.

The term "agent" as used herein describes any molecule, e.g. protein or non-protein organic or inorganic pharmaceutical. Agents of particular interest are those that modulate promoter activity. In certain cases, a plurality of assays is run in parallel with different agent concentrations to obtain a differential response to the various concentrations. One of these concentrations may serve as a negative control, i.e. at zero concentration or below the level of detection.

The terms "candidate agent", "test agent", "agent", "substance" and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 Da. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design.

Agents that modulate initiation of muscle cell atrophy may decrease expression of the secreted reporter enzyme and the first optically detectable protein by at least 10%, at least 20%, at least 30%, at least 40%, at least 50%, at least 60%, at least 70%, at least 80%, or at least 90%, or more, relative to controls that have not been exposed to the agent.

Agents that modulate promoter activity may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity, etc.

In Vivo Screening Assays

An in vivo screening assay is provided. In certain embodiments, the assay comprises identifying agents that alter production of the reporter protein encoded by the reporter construct using an animal model described above. The method may involve contacting the animal model with a candidate agent, and determining the effect of the agent on production of the reporter protein compared with production of the reporter protein in a control animal not treated with the agent.

In certain cases, the animal for may be subjected to a promoter-inducing stimulus before or after contacting the animal with a candidate agent. In certain embodiments, the animal for may be subjected to a promoter-inducing stimulus and contacted with a candidate agent simultaneously.

The animal is contacted with the candidate agent, e.g., the agent is administered to the animal by any acceptable route of administration, including, but not limited to, oral (e.g., oral gavage), intravenous, intramuscular, intranasal, subcutaneous, intragastric, etc., e.g., any enteral or parenteral route. A single dose is administered, or multiple doses over a period of time are administered.

In embodiments in which the construct system is designed to provide a read-out for muscle atrophy, animal may be subjected to an atrophy inducing stimuli before or after contacting the animal with a candidate agent. In certain embodiments, the animal model for muscle cell atrophy may be subjected to an atrophy inducing stimuli and contacted with a candidate agent simultaneously. A number of conditions known to induce atrophy may be used as an atrophy inducing stimuli, including but not limited to, glucocorticoid administration, starvation, cardiac failure, denervation, immobilization, sepsis, implanting hepatoma, streptozotocin-induced diabetes mellitus, nephrectomy, etc.

In embodiments in which a secreted reporter enzyme is used, the production of secreted reporter enzyme may be monitored in a body fluid, such as blood. For example, SEAP may be detected and quantified in blood drawn at certain time points after administration of a candidate agent. SEAP may be monitored by well known methods described in Nilsson E. E., et al., *Cancer Chemother. Pharmacol.*, 49:

93-100, 2002, Westfall S. D. and Skinner M. K., *Mol Cancer Ther* 2005, 4(11), etc., as well as, by using kits from Applied Biosystems, Clontech, Invivogen, for example.

In vivo imaging of fluorescent/luminescent reporter proteins has been used extensively. For example, Burdette J. E. in Journal of Mol. Endocrin., 40, 253-261, 2008, reviews utilizing computed tomography, magnetic resonance imaging, ultrasonography, positron emission tomography, single-photon emission computed tomography, etc., for in vivo imaging. Methods for using luciferases for real-time imaging of luciferase expression in live animals have been described (e.g., L. F. Greer, et al., Luminescence 17: 43-74, 2002). In vivo imaging of fluorescent proteins in live animals is described in, e.g., Hoffman, Cell Death and Differentiation (2002) 9, 786-789.

In particular embodiments, the production of reporter protein(s) may be monitored at different points before and after subjecting the animal model to a stimulus, e.g., a stimulus that induces muscle cell atrophy. Similarly, the effect of a candidate agent may be determined by measuring the reporter proteins at several time points. For example, the production of reporter protein(s) may be measured at time 0 hrs, 12 hrs, 24 hrs, 36 hrs, 48 hrs, 72 hrs, 120 hrs, 1 week, 2 week, 1 month, 2 months, 3 months, 5 months, etc., after contacting the cell with a candidate agent under conditions that induce expression of the reporter protein. In certain embodiments, the measurement of the reporter proteins may be complimented by measuring the expression of the atrogen gene(s), as well as measuring cell/fiber size, morphology, muscle strength, etc.

Agents that modulate promoter activity may decrease expression of the reporter protein by at least 10%, at least 20%, at least 30%, at least 40%, at least 50%, at least 60%, at least 70%, at least 80%, or at least 90%, or more, relative to controls that have not been exposed to the agent.

In certain embodiments, a candidate agent found to be effective in decreasing the production of the reporter protein(s), in vivo or in vitro, may be further assessed by administering it to an animal under conditions that induce a phenotype, e.g., muscle cell atrophy. The effectiveness of the candidate compound may be determined by measuring the time of onset of muscle cell atrophy phenotype as well as severity of the phenotype. In certain embodiments, the effectiveness of the candidate compound may be determined by measuring muscle weight, muscle strength, fiber cross sectional area, kinetic Muscle cell atrophy may be initiated by a number of stimuli including but not limited to fasting, ageing, diabetes, advanced cancer, renal failure, sepsis, cachexia, arthritis, osteoporosis, diabetes, denervation, immobilization, muscle unloading, spinal cord injury, glucocorticoid treatment, and the like. In vitro, muscle cell atrophy may be initiated by starving, exposure of cells to for example, glucocorticoids, or to viruses. experiments, etc.

In Vitro Assays

In some embodiments, in vitro methods for identifying agents that modulate the production of the reporter protein are provided. Cell-based methods generally involve contacting a cell that produces the reporter proteins with a candidate agent, and determining the effect, if any, of the candidate agent on the production of the reporter proteins as compared to a control cell not treated with the candidate agent.

In certain cases, the cell may be subject to conditions that induce the reporter protein (e.g., muscle cell atrophy-inducing conditions) prior to, after or simultaneous with contacting the cell with a candidate agent. Conditions that induce muscle cell atrophy in vitro, include, starvation, glucocorticoid exposure, viral infection, hypoxia, etc.

The production of reporter protein(s) may be monitored at different points before and after subjecting the cells to the stimulus. Similarly, the effect of a candidate agent may be determined by measuring the reporter proteins at several time points. For example, the production of reporter protein(s) may be measured at time 0 hrs, 2 hrs, 4 hrs, 8 hrs, 12 hrs, 24 hrs, 36 hrs, 48 hrs, 72 hrs, 120 hrs, 1 week, 2 week, and up to 1 month, after contacting the cell with a candidate agent.

As noted earlier, determining production of the secreted reporter enzyme, if used, may be by measuring activity of a secreted reporter enzyme in the cell culture medium. For example, when the secreted reporter enzyme is SEAP, its activity may be assayed by kits available from Applied Biosystems or Clontech, etc.

The optically detectable protein may be detected and its level quantitated by, for example, by a microscope, fluorescence activated cell sorter, fluorimeter, etc.

In certain embodiments, the measurement of the reporter proteins may be complimented by measuring the expression of the atrogen gene(s), as well as measuring cell/fiber size, morphology, etc.

Agents

Formulations, including pharmaceutical formulations, comprising an agent identified by a screening method presented herein, are provided. In general, a formulation comprises an effective amount of an agent. An "effective amount" means a dosage sufficient to produce a desired result, e.g., a decrease in production of the secreted reporter enzyme, the first optically detectable protein, MuRF1, or prevent further loss of muscle mass, etc.

Formulations

In the subject methods, the active agent(s) may be administered to the host using any convenient means capable of producing the desired result. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Unit dosage forms for oral administration such as syrups, elixirs, and suspensions may be provided wherein each dosage unit, for example, teaspoonful, tablespoonful, tablet, contains a predetermined amount of the composition containing one or more inhibitors. Similarly, unit dosage forms for injection such as intravenous, intramuscular administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., *Remington's Pharmaceutical Sciences*, Mack Publishing Company, Easton, Pa., 17th edition, 1985. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 1,000 µg or about 10,000 µg of an agent that produces a desired result can be administered in a single dose. Alternatively, a target dosage of an agent that produces a desired result can be considered to be about in the range of about 0.1-1000 µM, about 0.5-500 µM, about 1-100 µM, or about 5-50 µM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that produces a desired result is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated herein include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

A variety of hosts (wherein the term "host" is used interchangeably herein with the terms "subject" and "patient") are treatable according to the subject methods. Generally such hosts are "mammals" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts may be humans.

Utility

The methods and systems described above may be employed, for example, to identify compounds that modulate physiological process that can be read by gene expression. In certain embodiments, the method and system can be used to identify compounds that inhibit or stimulate a signal transduction pathway that is initiated by a stimulus in a cell type. The stimulus may be physical, chemical or environmental, for example, and the physiological process may be related to a disease (e.g., cancer, an inflammatory disease or a pathogen infection) or a condition (e.g., aging or muscle wasting) for example.

In one embodiment, the in vivo and in vitro models presented herein provide for methods to identify and test agents that may decrease muscle cell atrophy. These agents may be used in formulations that may be used to treat subjects with muscle cell atrophy. In addition, these agents may be given prophylactically to subjects at risk for developing muscle cell atrophy. A subject that may benefit from an agent identified by the methods provided herein may have or be at risk for developing muscle cell atrophy caused by a variety of stimuli. These stimuli include but are not limited to fasting, ageing, advanced cancer, renal failure, sepsis, cachexia, arthritis, osteoporosis, and diabetes. Atrophy of muscles may also be a result of their disuse or denervation, e.g., immobilization, muscle unloading, spinal cord injury, etc. In certain embodiments, the subject may have a health problem that is exacerbated by muscle cell atrophy, such as, HIV, chronic heart failure, chronic kidney disease, liver cirrhosis, burn injuries, osteoporosis, arthritis, etc. The methods of using cells and animal models to screen for candidate compounds that inhibit muscle cell atrophy may be used identify agents that improve protein content, fiber diameter, force production, and fatigue resistance of muscles in subjects with muscle cell atrophy. In one embodiment, a compound identified by the method described above may be employed to treat or prevent atrophy of the diaphragm during ventilator support after surgery, which occurs very rapidly.

EXAMPLES

The following examples are provided in order to demonstrate and further illustrate certain embodiments and aspects of the present invention and are not to be construed as limiting the scope thereof.

Example 1

General Description of Exemplary Reporter System

This exemplary system contains three component system (A, B & C) designed to amplify signals to a specific promoter and to restrict such reporter signals to a single tissue (even if promoter naturally expresses in other tissues). In the example shown, the reporter should be only expressed in muscle cells.

Amplification is accomplished by utilizing a two-step reporter configuration whereby the primary reporter drives the expression of a transcription factor (tTA) instead of directly driving a reporter gene such as luciferase (see component A). The tTA that gets produced during the primary promoter activity is then capable of directing a second transcriptional event based on a tTA response element driving a reporter protein (depicted below as Luciferase-2A-SEAP; see component C). This results in signal amplification since each given tTA produced by the primary promoter is capable of driving the production of many times its own number via transcription from the tetracycline promoter.

Tissue restriction is accomplished by dividing the transcription factor (tTA) into two parts, each fused to an intein-based protein trans-splicing element. Thus, the product produced by the primary promoter (tTA-VP16 transactivation domain; component A) is only functional when it is expressed in the presence of the rest of tTA (tTA-DNA binding domain; component B). The intein splicing elements sew these two halves together to reconstitute a fully functional tTA molecule. Tissue specific reporting can therefore be accomplished by using a well defined, tissue restricted promoter to drive expression one of the components in only the desired target tissue (e.g., muscle). Thus, even if the primary promoter (e.g., the Atrogin-1 promoter; see component A) has residual activity in other tissues, the reporter will readout only since this is the only tissue where both components are produced at the same time.

This approach can be configured to work as a 3 component set built into lentiviral, transposon or any other vector, e.g., viral, system. Transiently electroporating reporter plasmids into muscle or other tissue delivery methods can be employed if desirable. It can also be configured to function in the context of transgenic animals. Furthermore, this system can be configured to work with strategies that employ site-specific knock-in's of any of the critical elements to produce, for example, a atrogen gene that is operably linked (e.g., via an IRES or translational shunt sequence) to a nucleic acid that encodes one of the transcription factor components. Combinations of any of the above listed approaches are also possible. The method described here can be applied to any tissue type using a variety of strategies to restrict the expression of one component in the system such that full reconstitution occurs one in cells capable of expressing all the components of the reporter system.

Example 2

Description of Exemplary Constructs and Proof of Construct Experiments

Configuration 1A

Figure 2:
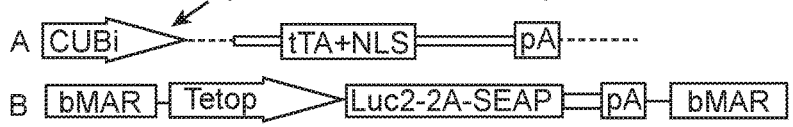
FIGS. 2-9 schematically illustrate various constructs that may be employed proof of concept experiments. Details of each of the illustrated constructs are set forth in the Examples section below.

FIG. 2 illustrates a two component system (A & B) designed to validate a method for amplifying signals using the Tetracycline transactivator (tTA). This test set will function as a positive control since it uses a constitutive promoter for component A and is designed to test the basic function of each of the components in the system. This test set mimics the configuration in a transgenic animal using the Atrogin-1 promoter and downstream applications (i.e. in applications in which the Atrogin-1 promoter replaces the CUBi promoter in component A listed below). Each component is intended to be constructed as a separate sleeping beauty vector (see Izsvak et al, J. Mol. Biol. 2000 302:93-102). This configuration should demonstrate that the ORF translates properly and tTA-NLS can be imported into the nucleus and activate the TetOP-Luciferase reporter system. This approach can be tested in transgenic animals (in which component A is a transgenic animal with a Atrogin-1-tTA cassette and component B is a transgenic animal with Tetop-Luc2-2A-SEAP reporter; where the final animal is produced by breeding animals A & B).

With reference to FIG. 2, CUBi is a fusion between the CMV immediate-early enhancer and the human Ubiqutin-B promoter (with a chimeric intron) to provide constitutive robust expression of the ORF (tTA-NLS). This configuration mimics the configuration that may be employed in a transgenic approach based on the Atrogin-1 promoter is utilized in later, downstream applications (i.e. an approach in which the Atrogin-1 promoter replaces the CUBi promoter in component A). Luc2-2A-SEAP is a bi-functional reporter in which luciferase provides a bioluminescence function and the SEAP (secretable alkaline phosphatase) portion providing for a simple blood-based assay. The components are separated by a translational shunt sequence. Tetop is the tTA targeted promoter. bMAR's are transcriptional insulators (from beta-Globulin gene) that are used to reduce integration-dependent basal transcription from the Tetop promoter.

Configuration 1B

Figure 3:
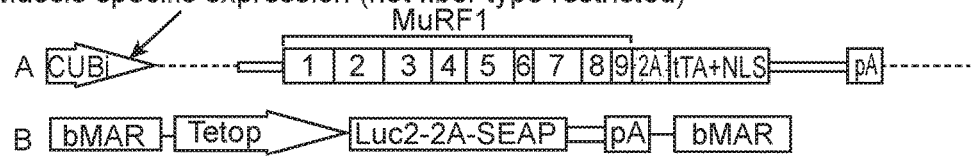

FIG. 3 illustrates a two component system (A & B) designed to validate a method for amplifying signals and for testing configurations based on C-terminal fusions to the MuRF1 protein. This test set is intended to mimic the configuration expected if a MuRF1-targeted knock-in approach is utilized in later, downstream transgenic applications. Each component is intended to be constructed as a separate sleeping beauty vector. The main goal of this configuration is to demonstrate the ORF translates properly, 2A shunts/cleaves away tTA-NLS, and tTA-NLS can import into the nucleus and activate the TetOP-Luciferase reporter system. This approach can be tested in transgenic animals (using a system in which component A is knock-in of 2A-tTA-NLS at c-terminus of MuRF1, component B is transgenic animal with Tetop-Luc2-2A-SEAP reporter, where the final animal is produced by breeding animals A & B).

With reference to FIG. 3, CUBi is a fusion between the CMV immediate-early enhancer and the human Ubiqutin-B promoter (with a chimeric intron) to provide constitutive robust expression of the ORF (MuRF1-2A-tTA-NLS). 2A is a ribosomal shunt site and allows post-translational separation of the tTA-NLS and the MuRF1 ORFs. This configuration mimics/approximates how the reporter ORF is fused to the c-terminus of MuRF1 in a knock-in animal. Luc2-2A-SEAP is a reporter, as described above. Tetop and bMAR's are described above.

Configuration 1C

Figure 4:
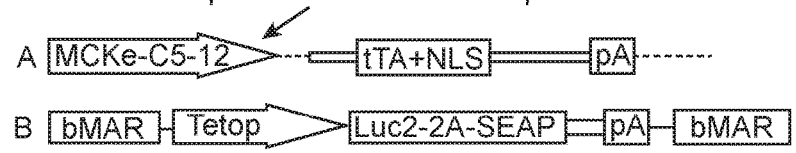

FIG. 4 illustrates a two component system that is identical to the configuration outlined for configuration 1A with the exception that a muscle specific MCKe-C5-12 promoter is utilized in component A. The tissue restricted expression of component A should allow systemic delivery methods (tail vein injection) to be used while preserving tissue specific expression of the reporter ORF. This configuration is a surrogate for the ultimate goal of having a MuRF1 and/or Atrogin-1 promoter driving the tTA-NLS ORF but nonetheless provides useful information for what to expect from a muscle specific promoter when using systemic deliver routes. Each component is intended to be constructed as a separate sleeping beauty vector. his approach can be tested in transgenic animals (in which component A is a transgenic animal with a Atrogin-1-tTA cassette; component B is a transgenic animal with Tetop-Luc2-2A-SEAP reporter; and the final animal is produced by breeding animals A & B).

All annotations for FIG. 4 are the same as for FIG. 2, except component A is driven by a muscle specific MCKe-C5-12 promoter. This allows the system to be tested using a tissue specific promoter with weaker expression levels relative to the CUBi configuration. The MCKe-C5-12 promoter offers constitutive expression in skeletal muscle (Wang, B et al. Gene Therapy 15, 1489-1499, 2008). This promoter is notable since it is compact AND seems to lack the type II fiber-specific profile associated with other forms of the MCK promoter. The tissue restricted expression of component A should allow systemic delivery methods (tail vein injection) to be used while preserving tissue specific expression of the reporter ORF. This configuration is a surrogate for the ultimate goal of having a MuRF1 and/or Atrogin-1 promoter driving the tTA-NLS ORF but nonetheless provides useful information for what to expect from a muscle specific promoter.

Configuration 1D

Figure 5:
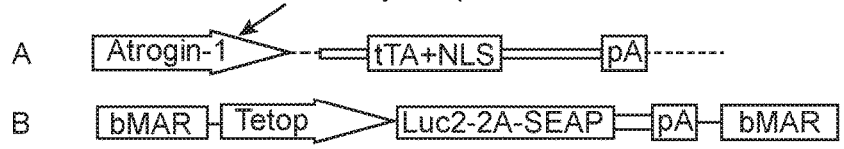

FIG. 5 illustrates a two component system (A & B) designed to validate a method for amplifying ATROPHIC signals using the Atrogin-1 promoter. Each component is intended to be constructed as a separate sleeping beauty vector. The main goal of this configuration is to demonstrate reporter expression ONLY AFTER the application of atrophic stimuli (denervation of muscle, hind limb suspension, glucocorticoid treatment). If these experiments prove successful, this approach would then transition from sleeping beauty/lenti to engineered animals (component A: transgenic based on Atrogin-1promoter-tTA-NLS; component B: transgenic animal with Tetop-Luc2-2A-SEAP reporter; final animal produced by breeding animals A & B).

All annotations for FIG. 4 are the same as for FIG. 2 except is driven by the Atrogin-1 promoter (murine 3.5 kb). This allows the system to be tested using a promoter specifically responsive to atrophic stimuli. These experiments will be useful for characterizing both the tissue specificity AND the strength of reporter induction after application of atrophic stimuli. The information gathered here will be used to help determine the configuration of future reporter animals. If these reporters prove sufficiently strong after atrophic stimulation AND HAVE both a low basal level of expression with good tissue restriction, then the sleeping beauty-based configuration may be utilized on it's own as a reporter system.

Configuration 2A

Figure 6:
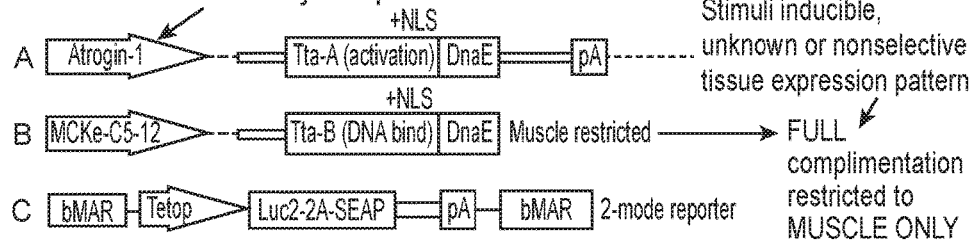

FIG. 6 illustrates a three component system (A, B & C) designed to validate a method for amplifying signals AND RESTRICTING such reporter signals to muscle (even if promoter naturally expresses in other tissues). Tissue-specific reporting is accomplished by splitting the actual reporter molecule (tTA) into two halves and restricting full complementation to MUSCLE ONLY. In this scenario, the target reporter promoter (MuRF1 or Atrogin-1) drives expression of one half of tTA fused to a trans-splicing intein protein (DnaE) [component A]. Since this portion of the reporter only encodes one half of the tTA molecule, no reporter signal would be expected to be generated based on the function of the driving promoter alone. Thus, even if the promoter utilized in component A had activity in skin or hair follicles, the reporter element (Tetop-Luciferase-2A-SEAP) [component C] would remain functionally silent in these tissues. To achieve signal in the desired tissue (muscle) only, a well characterized and tissue restricted promoter is utilized to drive the expression of the other half of the tTA molecule also fused to a trans-splicing element (DnaE) [component B]. In this configuration, only signals generated in muscle are registered since only muscle has the ability to generate the full compliment of both halves of tTA. This method could be generally applied to any reporter system in order to restrict signals to specific tissues and the avoid the potential complications associated with signal interference that might occur if the main promoter under study has less than ultra-specific expression patterns. Additionally, the system incorporates an amplification step by using a 2-step transcriptional-based (tTA) reporter system. This system should be compatible with transgenic-based reporter systems without the need to create knock-in animals.

With reference to FIG. 6, DnaE is a trans-splicing protein domain that can efficiently splice ORFs together post-translationally.

Configuration 2B

Figure 7:
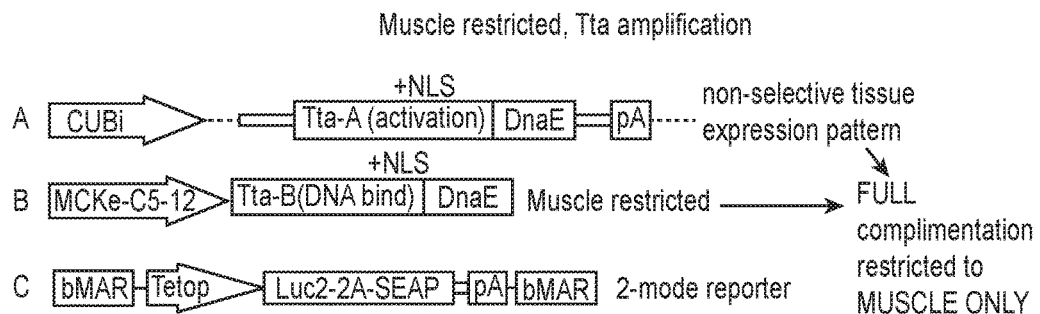

FIG. 7 illustrates a three component system (A, B & C) designed to validate a method for amplifying signals and restricting such reporter signals to muscle (even if promoter naturally expresses in other tissues). This version uses the constitutive CUBi promoter cassette in component A to validate the approach with a well characterized promoter without the need for induction via atrophic stimuli.

With reference to FIG. 7 DnaE is a trans-splicing protein domain that can efficiently splice ORFs together post-translationally.

Configuration 2C

Figure 8:
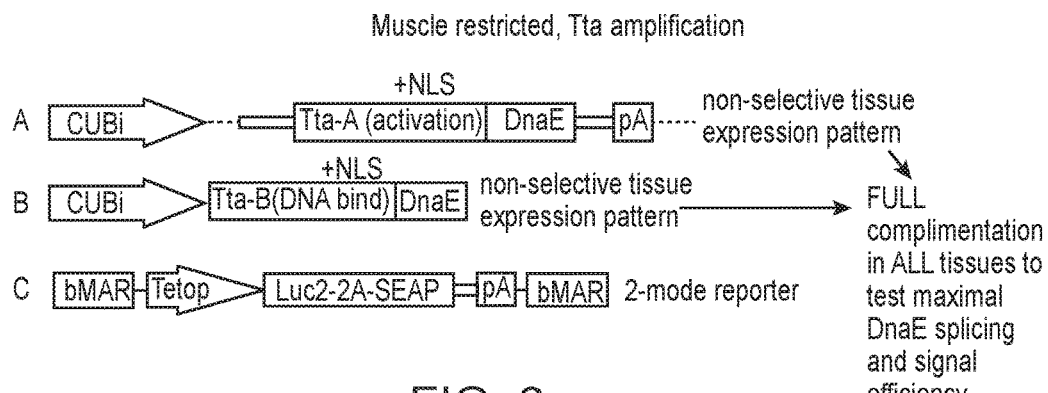

FIG. 8 illustrates a three component system (A, B & C) designed to validate a method for amplifying signals and restricting such reporter signals to muscle (even if promoter naturally expresses in other tissues). This version uses the constitutive CUBi promoter cassette in component A and B to validate the approach with a well characterized promoter without the need for induction via atrophic stimuli. This system validates the efficiency of the DnaE-trans splicing and signal generation under maximal expression conditions.

With reference to FIG. 8, DnaE is a trans-splicing protein domain that can efficiently splice ORFs together post-translationally.

Configuration 2D

Figure 9:
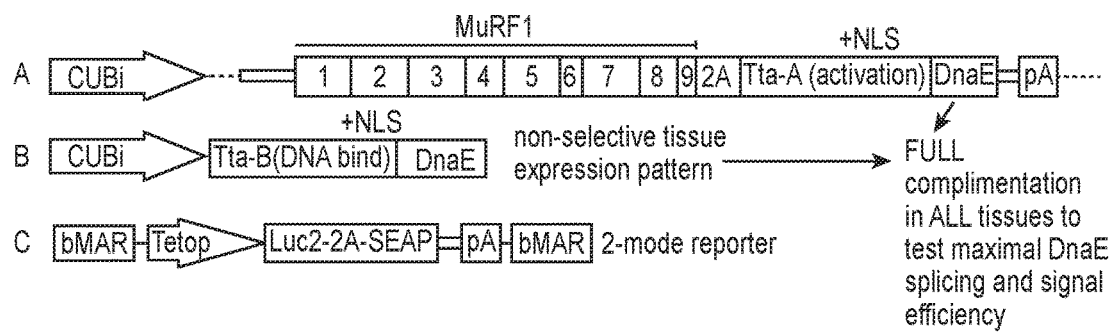

FIG. 9 illustrates a three component system (A, B & C) designed to validate a method for amplifying signals and restricting such reporter signals to muscle (even if promoter naturally expresses in other tissues). This version is for testing a configuration in which component A is fused to the c-terminus of MuRF1. This configuration should validate the approach prior to applying it to a knock-in animal.

With reference to FIG. 9, DnaE is a trans-splicing protein domain that can efficiently splice ORFs together post-translationally.

What is claimed is:

1. A construct system for expressing a reporter protein, comprising:
    a) a reporter construct comprising:
        i. an inducible promoter that is activated by a transcription factor; and
        ii. a coding sequence encoding a reporter protein, wherein said coding sequence is in operable linkage with said inducible promoter;
    b) a first transcription factor construct comprising:
        i. a first tissue-restricted promoter; and
        ii. a coding sequence encoding a first fusion protein comprising a first portion of a transcription factor and a first subunit of a split intein, wherein said coding sequence is in operable linkage with said first tissue-restricted promoter; and
    c) a second transcription factor construct comprising:
        i. a second tissue-restricted promoter; and
        ii. a coding sequence encoding a second fusion protein comprising a second portion of said transcription factor and a second subunit of said split intein, wherein the second subunit of said split intein specifically binds to the first subunit of the split intein and said coding sequence is in operable linkage with said second tissue-restricted promoter;
    wherein the interaction between the first and second fusion proteins encoded by the first and second transcription factor constructs is solely mediated by the first subunit of the split intein and the second subunit of the split intein,
    wherein the first and second tissue-restricted promoters are different and wherein expression of said first and second fusion proteins in a cell results in ligation, by a protein-splicing reaction mediated by said first and second subunits of said split intein, of said first and second portions of said transcription factor to produce said transcription factor and provides expression of the reporter protein only in tissues in which expression of the promoters overlap.

2. The construct system of claim 1, wherein said system provides for expression of said transcription factor only in regions in which expression of said promoters overlaps.

3. The construct system of claim 1, wherein said transcription factor has a portion of the GAL4, VP16 or the tetracycline activator.

4. The construct system of claim 1, wherein the promoter that is activated by said transcription factor comprises at least one binding site for GAL4 or the tetracycline activator.

5. The construct system of claim 1, wherein at least two of said constructs are present on the same vector.

6. The construct system of claim 1, wherein the constructs are present on different vectors.

7. The construct system of claim 1, wherein the reporter protein is optically detectable.

8. The construct system of claim 1, wherein the reporter protein comprises a luciferase.

9. The construct system of claim 1, wherein the reporter protein comprises a fluorescent protein.

10. An isolated cell or a cell of a non-human organism comprising the constructs system of claim 1.

11. The isolated cell or cell of a non-human organism of claim 10, wherein said cell is an animal cell.

12. The isolated cell or cell of a non-human organism of claim 11, wherein said cell is a mammalian cell.

13. The isolated cell or cell of a non-human organism of claim 10, wherein said first and second fusion proteins are expressed in said cell, thereby resulting in the expression of said reporter protein.

* * * * *